United States Patent
Bettarini et al.

[11] Patent Number: 5,821,197
[45] Date of Patent: Oct. 13, 1998

[54] ARYITHIADIAZOLONES WITH A HERBICIDAL ACTIVITY

[75] Inventors: Franco Bettarini; Piero La Porta, both of Novara; Sergio Massimini, Milan; Ernesto Signorini, Malnate; Domenico Portoso, Lodi, all of Italy

[73] Assignee: Isagro Ricerca S.r.l., Milan, Italy

[21] Appl. No.: 937,745

[22] Filed: Sep. 25, 1997

Related U.S. Application Data

[63] Continuation of Ser. No. 773,002, Dec. 23, 1996, abandoned.

[30] Foreign Application Priority Data

Dec. 21, 1995 [IT] Italy ................... MI95/A2705

[51] Int. Cl.⁶ .......... A01N 43/824; A01N 43/84; C07D 285/12; C07D 265/36
[52] U.S. Cl. .......... 504/263; 504/225; 544/105; 548/136
[58] Field of Search .......... 504/225, 263; 544/105; 548/136

[56] References Cited

U.S. PATENT DOCUMENTS

| | | |
|---|---|---|
| 3,746,719 | 7/1973 | Sasse . |
| 3,818,026 | 6/1974 | Boesch . |
| 3,971,803 | 7/1976 | Rosenberger et al. ........ 548/136 X |
| 4,943,583 | 7/1990 | Lüthy ........................ 548/136 X |
| 5,418,246 | 5/1995 | Bettarini et al. . |
| 5,550,140 | 8/1996 | Bettarini et al. . |

FOREIGN PATENT DOCUMENTS 0 274 249  7/1988  European Pat. Off. .

*Primary Examiner*—MIchael G. Ambrose
*Attorney, Agent, or Firm*—Oblon, Spivak, McClelland, Maier & Neustadt, P.C.

[57] ABSTRACT

Arylthiadiazolones having formula (I):

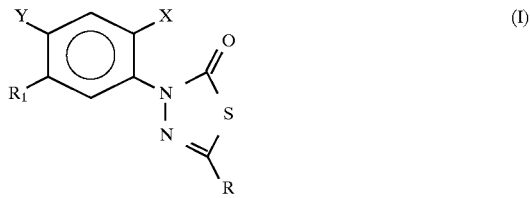

have a high herbicidal activity and are used for controlling weeds in agricultural cultivations.

23 Claims, No Drawings

ARYITHIADIAZOLONES WITH A HERBICIDAL ACTIVITY

This application is a Continuation of application Ser. No. 08/773,002, filed on Dec. 23, 1996, now abandoned, The present invention relates to new arylthiadiazolones.

More specifically the present invention relates to arylthiadiazolones having a high herbicidal activity, a process for their preparation and their use as herbicides for the control of weeds in agricultural crops.

Thiadiazolones having a herbicidal activity are described in U.S. Pat. Nos. 3.801.589, 3.746.719 and 3.776.919. These products however are not very selective as they are generally toxic also towards the most important agricultural cultivations.

The Applicant has now found new arylthiadiazolones which, as well as having a high herbicidal activity against numerous kinds of weeds, also have a low phytotoxicity for one or more cultivations of greatest agricultural interest and can therefore be used as selective herbicides.

The present invention therefore relates to arythiadiazolones having general formula (I):

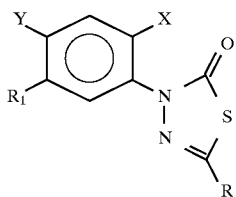

wherein:
R represents a $C_1$–$C_6$ alkyl or haloalkyl group linear or branched; a $C_3$–$C_6$ cycloalkyl or halocycloalkyl group; a $C_4$–$C_7$ cycloalkylalkyl or halocycloalkylalkyl group; a $C_2$–$C_6$ alkenyl or haloalkenyl group linear or branched;

X represents a hydrogen atom; a fluorine atom; a chlorine atom; a bromine atom, a methyl group;

Y represents a hydrogen atom, a halogen atom such as chlorine, fluorine, bromine or iodine; a $C_{1-C4}$ alkyl or haloalkyl group linear or branched; a$C_1$—$C_4$ alkoxy or haloalkoxy group linear or branched; a $C_1$–$C_4$ alkylthio or haloalkylthio group linear or branched; a $C_1$–$C_4$ alkylsulphonyl group linear or branched; a $C_1$–$C_4$ alkylsulphinyl group linear or branched; a cyano group; a nitro group;

$R_1$ represents a $C_1$–$C_8$ alkyl group linear or branched; a $C_1$–$C_8$ alkoxy group linear or branched; a $C_1$–$C_8$ alkylthio group linear or branched; a $C_3$–$C_6$ cycloalkoxy group; a $C_3$–$C_6$ cycloalkylthio group; a $C_4$–$C_8$ cycloalkylalkyl group; a $C_4$–$C_8$ cycloalkylalkoxy group; a $C_4$–$C_8$ cycloalkylalkylthio group; a $C_2$–$C_8$ alkenyl group linear or branched; a $C_2$–$C_8$ alkenyloxy group linear or branched; a $C_2$–$C_8$ alkenylthio group linear or branched; a $C_2$–$C_8$ alkinyl group linear or branched; a $C_3$–$C_8$ alkynyloxy group linear or branched; a $C_3$–$C_8$ alkynylthio group linear or branched; a $C_3$–$C_8$ alkynylsulphinyl group linear or branched; a $C_3$–$C_8$ alkynylsulphonyl group linear or branched; an OH group; an SH group; said groups in turn optionally substituted with one or more groups selected from halogen atoms such as chlorine, fluorine, bromine or iodine, $C_1$–$C_4$ alkyl or haloalkyl groups linear or branched; a $C_1$–$C_4$ alkoxy or haloalkoxy groups linear or branched; a $C_1$–$C_4$ alkylthio or haloalkylthio groups linear or branched;

or Y and $R_1$, jointly represent an O—$CH_2$–CO—$NR_4$ group wherein $R_4$ represents a hydrogen atom; a $C_1$–$C_8$ alkyl or haloalkyl group linear or branched; a $C_4$–$C_8$ cycloalkylalkyl or halocycloalkylalkyl group; a $C_2$–$C_8$ alkenyl or haloalkenyl group linear or branched; a $C_3$–$C_8$ alkynyl or haloalkynyl group linear or branched; a $C_5$–$C_8$ alkoxyalkynyl or haloalkoxyalkynyl group linear or branched.

The arylthiadiazolones having general formula (I) have a high herbicidal activity.

Arylthiadiazolones having general formula (I) which are preferred for their herbicidal activity are those wherein:
$R_1$ represents a $C_3$–$C_5$ alkynyloxy group; a $C_3$–$C_5$ alkynylthio group; a $C_3$–$C_5$ alkenyloxy group; a $C_3$–$C_5$ alkenylthio group, optionally substituted with halogen atoms.

Specific examples of arylthiadiazolones having general formula (I) which are interesting for their herbicidal activity are:

5-t-butyl-3-[2,4-dichloro-5-(prop-2ynyloxy)phenyl]-1,3,4-thiadiazol-2(3H)-one (Compound Nr. 1);

5-t-butyl-3-[5-(but-3-yn-2-yloxy)-2,4dichlorophenyl]-1,3,4-thiadiazol-2(3H)-one (Compound Nr. 2);

5-t-butyl-3-[4-chloro-2-fluoro-5-(prop-2ynyloxy) -phenyl]-1,3,4-thiadiazol-2(3H)-one (Compound Nr. 3);

5-t-butyl-3-[5-(but-3-yn-2-yloxy)-4chloro-2-fluorophenyl]-1,3,4-thiadiazol-2(3H)-one;

5-t-butyl-3-[2-chloro-4-fluoro-5-(prop-2-ynyloxy) -phenyl]-1,3,4-thiadiazol-2(3H)-one (Compound Nr. 4);

5-t-butyl-3-[5-(but-3-yn-2-yloxy)-2-chloro-4-fluorophenyl]-1,3,4-thiadiazol-2(3H)-one;

3-[4-bromo-2-chloro-5-(prop-2-ynyloxy)phenyl]-5-t-butyl-1,3,4-thiadiazol-2(3H) -one (Compound Nr. 5);

3-[4-bromo-5-(but-3-yn-2-yloxy)-2-chlorophenyl]-5-t-butyl-1,3,4-thiadiazol-2(3H)-one;

3-[4-bromo-2-fluoro-5-(prop-2-ynyloxy)phenyl]-5-t-butyl-1,3,4-thiadiazol-2(3H)-one (Compound Nr. 6);

3-[4-bromo-5-(but-3-yn-2-yloxy)-2-fluorophenyl]-5-t-butyl-1,3,4-thiadiazol-2(3H)-one;

5-cyclopropyl-3-[2,4-dichloro-5-(prop-2-ynyloxy) phenyl]-1,3,4-thiadiazol-2(3H)-one (Compound Nr. 7);

3-[5-(but-3-yn-2-yloxy)-2,4-dichlorophenyl]-5-cyclopropyl-1,3,4-thiadiazol-2(3H)-one (Compound Nr. 8);

5-cyclopropyl-3-[4-cloro-2-fluoro-5-(prop-2-ynyloxy) phenyl]-1,3,4-thiadiazol-2(3H)-one (Compound Nr. 9);

3-[5-(but-3-yn-2-yloxy)-4-chloro-2-fluorophenyl]-5-cyclopropyl-1,3,4-thiadiazol-2(3H)-one;

5-cyclopropyl-3-[2-chloro-4-fluoro-(5-prop-2-ynyloxy) phenyl]-1,3,4-thiadiazol-2(3H)-one (Compound Nr. 10);

3-[5-but-3-yn-2-yloxy)-2-chloro-4-fluorophenyl]-5-cyclopropyl-1,3,4-thiadiazol-2(3H)-one;

3-[4-bromo-2-chloro-5-(prop-2ynyloxy)phenyl]-5-cyclopropyl-1,3,4-thiadiazol-2(3H)-one (Compound Nr. 11);

3-[4-bromo-5-(but-3-yn-2-yloxy)-2chlorophenyl]-5-cyclopropyl-1,3,4-thiadiazol-2(3H)-one;

3-[4-bromo-2-fluoro-5-(prop-2ynyloxy)phenyl]-5-cyclopropyl-1,3,4-thiadiazol-2(3H)-one;

3-[4-bromo-5-(but-3-yn-2-yloxy)-2-fluorophenyl]-5-cyclopropyl-1,3,4-thiadiazol-2(3H)-one;

3-[2,4-dichloro-5-(prop-2-ynyloxy)phenyl]-5-ethyl -1,3,4-thiadiazol-2(3H)-one (Compound Nr. 12);

3-[5-(but-3-yn-2-yloxy)-2,4-dichlorophenyl]-5-ethyl-1,3,4-thiadiazol-2(3H)-one (Compound Nr. 13);

3-[4-chloro-2-fluoro-5-(prop-2-ynyloxy)phenyl]-5-ethyl-1,3,4-thiadiazol-2(3H)-one (Compound Nr. 14);

3-[5-(but-3-yn-2-yloxy)-4-chloro-2-fluorophenyl]-5-ethyl-1,3,4-thiadiazol-2(3H)-one;

3-[2,4-dichloro-5-(prop-2-ynyloxy)phenyl]-5-isopropyl-1,3,4-thiadiazol-2(3H)-one (Compound Nr. 15);

3-[5-(but-3-yn-2-yloxy)-2,4-dichlorophenyl]-5-isopropyl-1,3,4-thiadiazol-2(3H)-one (Compound Nr. 16);

3-[4-chloro-2-fluoro-5-(prop-2-ynyloxy)phenyl]-5-isopropyl-1,3,4-thiadiazol-2(3H)-one (Compound Nr. 17);

3-[5-(but-3-yn-2-yloxy)-4-chloro-2-fluorophenyl]-5-isopropyl-1,3,4-thiadiazol-2(3H)-one (Compound Nr. 18);

3-[2,4-dichloro-5-(prop-2-ynyloxy)phenyl]-5-(1-methylcyclopropyl)-1,3,4-thiadiazol-2(3H)-one (Compound Nr. 19);

3-[4-chloro-2-fluoro-5-(prop-2-ynyloxy)phenyl]-5-(1-methylcyclopropyl)-1,3,4-thiadiazol-2(3H)-one (Compound Nr. 20);

5-sec-butyl-3-[2,4-dichloro-5-(prop-2-ynyloxy)phenyl]-1,3,4-thiadiazol-2(3H)-one (Compound Nr. 21);

5-sec-butyl-3-[2-chloro-4-fluoro-5-(prop-2-ynyloxy)phenyl]-1,3,4-thiadiazol-2(3H)-one (Compound Nr. 22);

3-[2,4-dichloro-5-(prop-2-ynyloxy)phenyl]-5-(2-methylbut-2-yl)-1,3,4-thiadiazol-2(3H)-one (Compound Nr. 23);

3-[2-chloro-4-fluoro-5-(prop-2-ynyloxy)phenyl]-5-(2-methylbut-2-yl)-1,3,4-thiadiazol-2(3H)-one (Compound Nr. 24);

3-[2,4-dichloro-5-(prop-2-ynyloxy)phenyl]-5-(1-methylethenyl)-1,3,4-thiadiazol-2(3H)-one (Compound Nr. 25);

3-[4-chloro-2-fluoro-5-(prop-2-ynyloxy)phenyl]-5-(1-methylethenyl)-1,3,4-thiadiazol-2-(3H)-one (Compound Nr. 26);

5-t-butyl-3-[2,4-dichloro-5-(prop-2-ynylthio)phenyl]-1,3,4-thiadiazol-2(3H)-one (Compound Nr. 27);

5-t-butyl-3-[5-(but-3-yn-2-ylthio)-2,4-dichlorophenyl]-1,3,4-thiadiazol-2(3H)-one (Compound Nr. 28);

5-t-butyl-3-[4-chloro-2-fluoro-5-(prop-2-ynylthio) phenyl]-1,3,4-thiadiazol-2(3H)-one (Compound Nr. 29);

5-t-butyl-3-[5-(but-3-yn-2-ylthio)-4-chloro-2-fluorophenyl]-1,3,4-thiadiazol-2(3H)-one (Compound Nr. 30);

5-cyclopropyl-3-[2,4-dichloro-5-(prop-2-ynylthio)phenyl]-1,3,4-thiadiazol-2(3H)-one;

3-[5-(but-3-yn-2-ylthio)-2,4-dichlorophenyl]-5-cyclopropyl-1,3,4-thiadiazol-2(3H)-one;

5-cyclopropyl-3-[4-chloro-2-fluoro-5-(prop-2-ynylthio) phenyl]-1,3,4-thiadiazol-2(3H)-one;

3-[5-(but-3-yn-2-ylthio)-4-chloro-2-fluorophenyl]-5-cyclopropyl-1,3,4-thiadiazol-2(3H)-one;

5-t-butyl-3-[4-chloro-2-methyl-5-(prop-2-ynyloxy)phenyl]-1,3,4-thiadiazol-2(3H)-one (Compound Nr. 31);

5-cyclopropyl-3-[4-chloro-2-methyl-5-(prop-2-ynyloxy) phenyl]-1,3,4-thiadiazol-2(3H)-one (Compound Nr. 32);

5-t-butyl-3-[5-(but-2-ynyloxy)-2,4-dichlorophenyl]-1,3,4-thiadiazol-2(3H)-one (Compound Nr. 33);

5-t-butyl-3-[5-(but-2-ynyloxy)-4-chloro-2-fluorophenyl]-1,3,4-thiadiazol-2(3H)-one (Compound Nr. 34);

3-[5-(but-2-ynyloxy)-2,4-dichlorophenyl]-5-cyclopropyl-1,3,4-thiadiazol-2(3H)-one (Compound Nr 35);

3-[5-(but-2-ynyloxy)-4-chloro-2-fluorophenyl]-5-cyclopropyl-1,3,4-thiadiazol-2(3H)-one (Compound Nr. 36);

5-t-butyl-3-[5-(3-chloroprop-2-ynyloxy)-2,4-dichlorophenyl]-1,3,4-thiadiazol-2(3H)-one (Compound Nr. 37);

5-cyclopropyl-3-[5-(3-chloroprop-2-ynyloxy)-2,4-dichlorophenyl]-1,3,4-thiadiazol-2(3H)-one (Compound Nr. 38);

5-t-butyl-3-[2,4-dichloro-5-(prop-2-enyloxy)phenyl]-1,3,4-thiadiazol-2(3H)-one (Compound Nr. 39);

5-t-butyl-3-[4-chloro-2-fluoro-5-(prop-2-enyloxy)-phenyl]-1,3,4-thiadiazol-2(3H)-one (Compound Nr. 40);

5-cyclopropyl-3-[2,4-dichloro-5-(prop-2-enyloxy)-phenyl]-1,3,4-thiadiazol-2(3H)-one;

5-cyclopropyl-3-[4-chloro-2-fluoro-5-(prop-2-enyloxy) phenyl]-1,3,4-thiadiazol-2(3H)-one;

5-t-butyl-3-[2,4-dichloro-5-(3,3-dichloroprop-2-enyloxy) phenyl]-1,3,4-thiadiazol-2(3H)-one (Compound Nr. 41);

5-t-butyl-3-[4-chloro-5-(3,3-dichloroprop-2-enyloxy)-2-fluorophenyl]-1,3,4-thiadiazol-2(3H)-one (Compound Nr. 42);

5-cyclopropyl-3-[2,4-dichloro-5-(3,3-dichloroprop-2-enyloxy)phenyl]-1,3,4-thiadiazol-2(3H)-one;

5-cyclopropyl-3-[4-chloro-5-(3,3-dichloroprop-2-enyloxy)-2-fluorophenyl]-1,3,4-thiadiazol-2(3H) -one;

5-t-butyl-3-[7-chloro-3,4-dihydro-4-(prop-2-ynyl)-2H-1,4-benzoxazin-3-onyl]-1,3,4-thiadiazol-2(3H)-one (Compound Nr. 43);

5-t-butyl-3-[7-fluoro-3,4-dihydro-4-(prop-2-ynyl)-2H-1,4-benzoxazin-3-onyl]-1,3,4-thiadiazol-2(3H)-one (Compound Nr. 44);

5-t-butyl-3-[2-chloro-5-(prop-2-ynyloxy)phenyl]-1,3,4-thiadiazol-2(3H)-one (Compound Nr. 45);

5-t-butyl-3-[4-chloro-5-(prop-2-ynyloxy)phenyl]-1,3,4-thiadiazol-2(3H)-one (Compound Nr. 46);

3-[2-bromo-4-chloro-5-(prop-2-ynyloxy)phenyl]-5-t-butyl-1,3,4-thiadiazol-2(3H)-one (Compound Nr. 47);

5-t-butyl-3-[2-chloro-4-cyano-5-(prop-2-ynyloxy)-phenyl]-1,3,4-thiadiazol-2(3H)-one (Compound Nr. 49);

5-t-butyl-3-[2-chloro-5-(prop-2-ynyloxy)-4-trifluoromethylphenyl]-1,3,4-thiadiazol-2(3H)-one (Compound Nr. 50).

A further object of the present invention is a process for the preparation of the compounds having general formula (I).

The compounds having general formula (I) can be obtained by means of a process which comprises the reaction of a thiohydrazide having general formula (II):

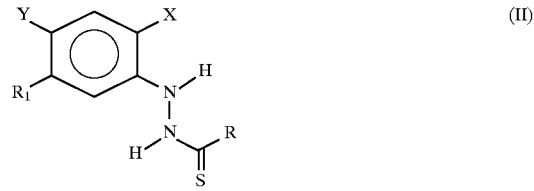

wherein R, X, Y and $R_1$ have the same meanings described above, with a cyclizing agent having general formula (III):

wherein:

L represents a chlorine atom; a $C_1$–$C_4$ alkoxy group linear or branched; a phenoxy group;

L' represents a chlorine atom; a $C_1$–$C_4$ alkoxy group linear or branched; a phenoxy group; or, when L represents a chlorine atom, L' represents a trichloromethoxy group or a benzyloxy group.

The above cyclization reaction can take place in a single step or in two steps depending on the type of cyclizing agent used.

Cyclizing agents which can be used for the purpose are phosgene, trichloromethylchloroformate (diphosgene), or an alkylchloroformate such as, for example, methylchloroformate or ethylchloroformate, benzylchloroformate, phenylchloroformate, etc.

When phosgene or trichloromethylchloroformate is used as cyclizing agent, the above cyclization reaction is carried out in a single step. For this purpose, the thiohydrazide having general formula (II), dissolved or suspended in a suitable inert organic solvent, is treated with the cyclizing agent, optionally dissolved in turn in a suitable inert organic solvent, at a temperature of between 20° C. and the boiling point of the mixture itself, optionally in the presence of an inorganic or organic base.

Inert organic solvents which can be used for the purpose are chlorinated hydrocarbons (such as, for example, methylene chloride, chloroform, 1,2-dichloroethane, etc.); aromatic hydrocarbons (such as, for example, benzene, toluene, xylene, etc.); chlorinated aromatic hydrocarbons (such as, for example, chlorobenzene, etc.); ethers (such as for example, ethyl ether, tetrahydrofuran, dioxane, etc.); esters (such as, for example, ethyl acetate, etc.).

Bases which can be used for the purpose are inorganic bases such as, for example, sodium bicarbonate, sodium hydroxide, sodium carbonate, sodium hydride, potassium hydroxide, potassium carbonate, or organic bases such as, for example, triethylamine, pyridine, 4-dimethylaminopyridine, etc.

When an alkyl, benzyl or phenylchloroformate are used as cyclizing agent, the cyclization reaction is generally carried out in two steps. For this purpose the thiohydrazide having general formula (II), dissolved or suspended in an inert organic solvent (selected from those listed above), is treated with the ester of chloroformic acid, in the presence of an inorganic or organic base (selected from those listed above), at a temperature of between 0° C. and the boiling point of the mixture itself, obtaining the intermediate having general formula (IV):

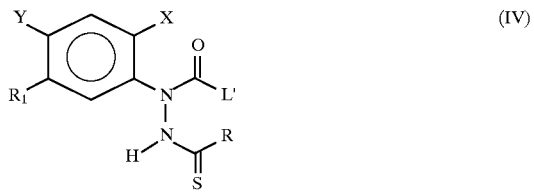

(IV)

wherein R, X, Y and $R_1$ have the same meanings described above and L' represents a $C_1$–$C_4$ alkoxy group linear or branched, a phenoxy group or a benzyloxy group, which is subsequently cyclized by heating to a temperature of between 120° C. and 200° C., optionally in the presence of a high-boiling organic solvent such as, for example, xylene or ortho-dichlorobenzene, and a base such as, for example, 4-dimethylaminopyridine, analogously to what is described in "Journal of Heterocyclic Chemistry" (1986), Vol. 23, pages 417–419.

The thiohydrazides having general formula (II) can be prepared according to known methods such as those described in "Beilstein" 15, Vol. II, page 92 and page 94 and Vol. III, page 156; in "Acta Chemica Scandinavica", Vol. 6 (1952), page 957 and Vol. 15 (1961), page 1097; in "Journal of Heterocyclic Chemistry", Vol. 17 (1980), page 191 and Vol. 23 (1986) page 417; in "Journal of Fluorine Chemistry", Vol. 12 (1978), pages 1–21; in "Chemistry Express", Vol. 6 (1991), page 411. For example, most of the thiohydrazides having general formula (II) can be conveniently prepared starting from the corresponding hydrazides by thionation with phosphorous pentasulfide or with the Lawesson reagent. The hydrazides can in turn be easily prepared by reaction of arylhydrazine suitably substituted with acyl chlorides.

The compounds having general formula (I) wherein $R_1$ represents an ether group linked to the aryl by means of the oxygen atom, can be alternatively prepared by the etherification of a 5-hydroxyarylthiadiazolone having general formula (V):

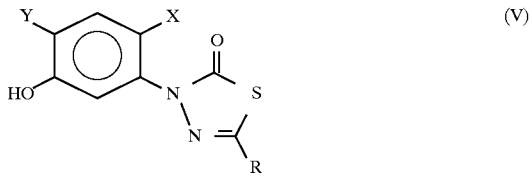

(V)

wherein R, X and Y have the same meanings described above, with a compound having general formula (VI):

Z—$R_1'$ (VI)

wherein:
Z represents a halogen atom, preferably chlorine or bromine, or an R'SO$_2$O group wherein R' represents a $C_1$–$C_4$ alkyl or haloalkyl group linear or branched or a phenyl group also optionally substituted with $C_1$–$C_3$ alkyl groups linear or branched, nitro groups, halogen atoms such as chlorine, fluorine or bromine;

$R_1'$ represents a $C_1$–C8 alkyl group linear or branched, a $C_3$–$C_6$ cycloalkyl group, a $C_4$–$C_8$ cycloalkylalkyl group, a $C_2$–C8 alkenyl group linear or branched, a $C_3$–$C_8$ alkynyl group linear or branched, all groups in turn optionally substituted by halogen atoms, $C_1$–$C_4$ alkyl or haloalkyl groups linear or branched, $C_1$–$C_4$ alkoxy or haloalkoxy groups linear or branched, $C_1$–$C_4$ alkylthio or haloalkylthio groups linear or branched.

The etherification reaction can be advantageously carried out in the presence of an inert organic solvent and in the presence of an organic or inorganic base, at a temperature of between −10° C. and the boiling point of the solvent used, preferably between 0° C. and 100° C.

Inert organic solvents which can be used for the purpose are, for example, benzene, toluene, xylene, acetone, methylethylketone, methylpropylketone, ethyl acetate, dimethoxyethane, diisopropylether, tetrahydrofuran, dioxane, acetonitrile, N,N-dimethylformamide, N,N-dimethylacetamide, N-methylpyrrolidone, dimethylsulfoxide.

Inorganic bases which can be used for the purpose are, for example, hydroxides and carbonates of sodium, potassium, calcium.

Organic bases which can be used for the purpose are, for example, triethylamine, pyridine, 4-dimethylaminopyridine, diazabicyclooctane (DABCO), diazabicycloundecene (DBU).

The 5-hydroxyarylthiadiazolones having formula (V) can be prepared from the arylthiadiazolones having formula (I), wherein $R_1$ represents a $C_1$–$C_4$ alkoxy group (for example, an isopropoxy group), by treatment with aluminum chloride.

The compounds having general formula (I) of the present invention have shown a high herbicidal activity which makes them suitable for use in the agricultural field in the defence of useful cultivations against weeds.

In particular, the compounds having general formula (I) are efficient in the control, both in pre-emergence and post-emergence, of numerous monocotyledon and dicotyledon weeds. At the same time, these compounds are compatible or have no toxic effects with respect to useful crops, both in pre-emergence and post-emergence treatment.

Examples of weeds which can be effectively controlled using the compounds having general formula (I) of the present invention are: *Solanum nigrum, Echinocloa crusgalli, Echinocloa oryzicola, Avena fatua, Ipomea spp., Abutilon theofrasti, Polygonum persicaria, Convolvulus sepium, Amaranthus retroflexus, Chenopodium Album Galium aparine, Papaver rhoaes, Alopercurus myosuroides, Cyperus spp., Panicum dichotomiflorum, Setaria viridis, Heteranthera spp. Portulaca oleracea, Digitaria sanquinalis, Capsella bursa pastoris, Monochoria vaginalis, Rotala indica, Scirpus juncoides, Sagittaria pygmaea*, etc.

With the dosages used for agricultural applications, the above compounds have shown no toxic effects towards important agricultural crops such as rice (*Oryza sativa*), wheat (*Triticum spp.*), maize (*Zea mais*), soybean (*Glycine max*), etc.

A further object of the present invention relates to a method for controlling weeds in cultivated areas by the application of the compounds having general formula (I).

The amount of compound to be applied to obtain the desired effect can vary depending on different factors such as, for example, the compound used, the crop to be preserved, the weed to be eliminated, the degree of infestation, climatic conditions, characteristics of the soil, method of application, etc.

Dosages of compound of between 1 g and 1000 g per hectare generally provide sufficient control.

For practical uses in agriculture it is often advantageous to use compositions with a herbicidal activity containing, as active substance, one or more compounds having general formula (I).

It is possible to use compositions in the form of dry powders, wettable powders, emulsifiable concentrates, microemulsions, pastes, granules, solutions, suspensions etc.: the selection of the type of composition will depend on the specific use.

The compositions are prepared according to the known methods, for example by diluting or dissolving the active substance with a solvent and/or solid diluent, possibly in the presence of surfactants.

As solid inert diluents, or carriers, it is possible to use kaolin, alumina, silica, talc, bentonite, chalk, quartz, dolomite, attapulgite, montmorillonite, diatomaceous earth, cellulose, starch, etc.

As liquid inert diluents, in addition to water obviously, it is possible to use organic solvents such as aromatic hydrocarbons (xylols, mixtures of alkylbenzols, etc.), aliphatic hydrocarbons (hexane, cyclohexane, etc.), halogenated aromatic hydrocarbons (chlorobenzol, etc.), alcohols (methanol, propanol, butanol, octanol, etc.), esters (isobutyl acetate, etc.), ketones (acetone, cyclohexanone, acetophenone, isophorone, ethylamylketone, etc.) or vegetable or mineral oils or their mixtures, etc.

As surfactants it is possible to use wetting and emulsifying agents of the non-ionic type (polyethoxylated alkylphenols, polyethoxylated fatty alcohols, etc.), anionic type (alkylbenzenesulfonates, alkylsulfonates, etc.), cationic type (quaternary salts of alkylammonium, etc.).

It is also possible to add dispersing agents (for example lignin and its salts, derivatives of cellulose, alginates, etc.), stabilizers (for example anti-oxidants, ultraviolet-ray absorbers, etc.).

To increase the range of action of the above compositions, other active ingredients can also be added such as, for example, other herbicides, fungicides, insecticides or acaricides, fertilizers.

The concentration of active substance in the above compositions can vary within a wide range, depending on the active compound, the applications for which they are destined, environmental conditions and type of formulation adopted.

The concentration of active substance is generally between 1% and 90%, preferably between 5% and 50%.

The following examples are illustrative and do not limit the scope of the present invention.

EXAMPLE 1

Preparation of N'-[2,4-dichloro-5-(prop-2-ynyloxy) phenyl]-N-thiopivaloyl-hydrazine Phosphorous pentasulfide ($P_4S_{10}$: 0.720 g, 1.6 mmoles) is added to a solution of N'-[2,4-dichloro-5-(prop-2-ynyloxy) phenyl]-N-pivaloyl-hydrazine (2 g; 6.4 mmoles) in dioxane (40 ml) and the mixture is heated to 60° C. for 3 hours. The mixture is then poured into water and extracted with ethyl ether. The organic phase is washed again with water, anhydrified with sodium sulfate and concentrated. The residue (2.8 g) is dissolved in ethyl ether/hexane 1:1, filtered on silica gel, concentrated and recrystallized from hexane. 1.7 g of product are obtained with a melting point of 126°–128° C.

EXAMPLE 2

Preparation of 5-t-butyl-3-[2,4-dichloro-5-(prop-2-ynyloxy)phenyl]-1,3,4-thiadiazol-2(3H)-one
(Compound Nr. 1)

Three drops of pyridine and 0.5 g (2.5 mmoles) of trichloromethylchloroformate are added to a solution of 1.65 g (5 mmoles) of N'-[2,4-dichloro-5-(prop-2-ynyloxy)-phenyl]-N-thiopivaloylhydrazine, obtained as described in Example 1, in 25 ml of dioxane, maintained in a nitrogen atmosphere. The reaction mixture is stirred, at room temperature, for 3 hours.

The mixture is poured into water (250 ml) and extracted with ethyl ether (3×100 ml). The organic phase is washed to neutrality with a saturated solution of sodium chloride, anhydrified with sodium sulfate and concentrated by means of a rotovapor. The raw product is purified by silica gel chromatography eluating with n-hexane/ethyl acetate in a ratio of 9:1.

1.4 g of a solid product are obtained corresponding to Compound Nr. 1 having a melting point of 92° C.

EXAMPLE 3

Operating analogously as described in Example 2, the following compounds were prepared starting from the corresponding thiohydrazides and using trichloromethylchloroformate or phosgene as cyclizing agent:

5-t-butyl-3-[5-(but-3-yn-2-yloxy)-2,4-dichlorophenyl]-1,3,4-thiadiazol-2(3H)-one (m.p. 100°–102° C.; compound Nr. 2);

5-t-butyl-3-[4-chloro-2-fluoro-5-(prop-2-ynyloxy)-phenyl]-1,3,4-thiadiazol-2(3H)-one (m.p. 73°–75° C.; compound Nr. 3);

5-t-butyl-[3-(2-chloro-4-fluoro-5-(prop-2-ynyloxy)-phenyl]-1,3,4-thiadiazol-2(3H)-one (compound Nr. 4);

3-[4-bromo-2-chloro-5-(prop-2-ynyloxy)phenyl]-5-t-butyl-1,3,4-thiadiazol-2(3H)-one (compound Nr. 5);

3-[4-bromo-2-fluoro-5-(prop-2-ynyloxy)phenyl]-5-t-butyl-1,3,4-thiadiazol-2(3H)-one (compound Nr. 6);

5-cyclopropyl-3-[2,4-dichloro-5-(prop-2-ynyloxy)-phenyl]-1,3,4-thiadiazol-2(3H)-one (m.p. 99°–101° C.; compound Nr. 7);

3-[5-(but-3-yn-2-yloxy)-2,4-dichlorophenyl]-5-cyclopropyl-1,3,4-thiadiazol-2(3H)-one (m.p. 109°–110° C.; compound Nr. 8);

5-cyclopropyl-3-[4-cloro-2-fluoro-5-(prop-2-ynyloxy) phenyl]-1,3,4-thiadiazol-2(3H)-one (compound Nr. 9);

5-cyclopropyl-3-[2-chloro-4-fluoro-(5-prop-2-ynyloxy) phenyl]-1,3,4-thiadiazol-2(3H)-one (compound Nr. 10);

3-[4-bromo-2-chloro-5-(prop-2-ynyloxy)phenyl]-5-cyclopropyl-1,3,4-thiadiazol-2(3H)-one (compound Nr. 11);

3-[2,4-dichloro-5-(prop-2-ynyloxy)phenyl]-5-ethyl -1,3,4-thiadiazol-2(3H)-one (m.p. 98°–100° C.; compound Nr. 12);

3-[5-(but-3-yn-2-yloxy)-2,4-dichlorophenyl]-5-ethyl-1,3,4-thiadiazol-2(3H)-one (m.p. 69°–71° C. compound Nr. 13);

3-[4-chloro-2-fluoro-5-(prop-2-ynyloxy)phenyl]-5-ethyl-1,3,4-thiadiazol-2(3H)-one (m.p. 92°–94° C. compound Nr. 14);

3-[2,4-dichloro-5-(prop-2-ynyloxy)phenyl]-5-isopropyl-1,3,4-thiadiazol-2(3H)-one (m.p. 55°–57° C.; compound Nr. 15);

3-[5-(but-3-yn-2-yloxy)-2,4-dichlorophenyl]-5-isopropyl-1,3,4-thiadiazol-2(3H)-one (m.p. 72°–74° C.; compound Nr. 16);

3-[4-chloro-2-fluoro-5-(prop-2-ynyloxy)phenyl]-5-isopropyl-1,3,4-thiadiazol-2(3H)-one (compound Nr. 17);

3-[5-(but-3-yn-2-yloxy)-4-chloro-2-fluorophenyl]-5-isopropyl-1,3,4-thiadiazol-2(3H)-one (compound Nr. 18);

3-[2,4-dichloro-5-(prop-2-ynyloxy)phenyl]-5-(1-methylcyclopropyl)-1,3,4-thiadiazol-2(3H)-one (compound Nr. 19);

3-[4-chloro-2-fluoro-5-(prop-2-ynyloxy)phenyl]-5 (1-methylcyclopropyl)-1,3,4-thiadiazol-2(3H)-one (compound Nr. 20);

5-sec-butyl-3-[2,4-dichloro-5-(prop-2-ynyloxy) phenyl]-1,3,4-thiadiazol-2(3H)-one (compound Nr. 21);

5-sec-butyl-3-[2-chloro-4-fluoro-5-(prop-2-ynyloxy) phenyl]-1,3,4-thiadiazol-2(3H)-one (compound Nr. 22);

3-[2,4-dichloro-5-(prop-2-ynyloxy)phenyl]-5-(2-methylbut-2-yl)-1,3,4-thiadiazol-2(3H)-one (compound Nr. 23);

3-[2-chloro-4-fluoro-5-(prop-2-ynyloxy)phenyl]-5-(2-methylbut-2-yl)-1,3,4-thiadiazol-2(3H)-one (compound Nr. 24);

3-[2,4-dichloro-5-(prop-2-ynyloxy)phenyl]-5-(1-methylethenyl)-1,3,4-thiadiazol-2(3H)-one (compound Nr. 25);

3-[4-chloro-2-fluoro-5-(prop-2-ynyloxy)phenyl]-5-(1-methylethenyl)-1,3, 4-thiadiazol-2-(3H)-one (compound Nr. 26);

5-t-butyl-3-[2,4-dichloro-5-(prop-2-ynylthio)phenyl]-1,3,4-thiadiazol-2(3H)-one (compound Nr. 27);

5-t-butyl-3-[5-(but-3-yn-2-ylthio)-2,4-dichlorophenyl]-1,3,4-thiadiazol-2(3H)-one (compound Nr. 28);

5-t-butyl-3-[4-chloro-2-fluoro-5-(prop-2-ynylthio)phenyl]-1,3,4-thiadiazol-2(3H)-one (compound Nr. 29);

5-t-butyl-3-[5-(but-3-yn-2-ylthio)-4-chloro-2-fluorophenyl] -1,3,4-thiadiazol-2(3H)-one (compound Nr. 30);

5-t-butyl-3-[4-chloro-2-methyl-5-(prop-2-ynyloxy)phenyl]-1,3,4-thiadiazol-2(3H)-one (compound Nr. 31);

5-cyclopropyl-3-[4-chloro-2-methyl-5-(prop-2-ynyloxy) phenyl]-1,3,4-thiadiazol-2(3H)-one (compound Nr. 32);

5-t-butyl-3-[5-(but-2-ynyloxy)-2,4-dichlorophenyl]-1,3,4-thiadiazol-2(3H)-one (compound Nr. 33);

5-t-butyl-3-[5-(but-2-ynyloxy)-4-chloro-2-fluorophenyl]-1, 3,4-thiadiazol-2(3H)-one (compound Nr. 34);

3-[5-(but-2-ynyloxy)-2,4-dichlorophenyl]-5-cyclopropyl-1, 3,4-thiadiazol-2(3H)-one (compound Nr. 35);

3-[5-(but-2-ynyloxy)-4-chloro-2-fluorophenyl]-5-cyclopropyl-1,3,4-thiadiazol-2(3H)-one (compound Nr. 36);

5-t-butyl-3-[5-(3-chloroprop-2-ynyloxy)-2,4-dichlorophenyl]-1,3,4-thiadiazol-2(3H)-one (compound Nr. 37);

5-cyclopropyl-3-[5-(3-chloroprop-2-ynyloxy)-2,4-dichlorophenyl]-1,3,4-thiadiazol-2(3H)-one (compound Nr. 38);

5-t-butyl-3-[2,4-dichloro-5-(prop-2-enyloxy)phenyl]-1,3,4-thiadiazol-2(3H)-one (compound Nr. 39);

5-t-butyl-3-[4-chloro-2-fluoro-5-(prop-2-enyloxy) phenyl]-1,3,4-thiadiazol-2(3H)-one (compound Nr. 40);

5-t-butyl-3-[2,4-dichloro-5-(3,3-dichloroprop-2-enyloxy) phenyl]-1,3,4-thiadiazol-2(3H)-one (compound Nr. 41);

5-t-butyl-3-[4-chloro-5-(3,3-dichloroprop-2-enyloxy)-2-fluorophenyl]-1,3,4-thiadiazol-2(3H)-one (compound Nr. 42);

5-t-butyl-3-[7-chloro-3,4-dihydro-4-(prop-2-ynyl) -2H-1,4-benzoxazin-3-onyl]-1,3,4-thiadiazol-2(3H)-one (compound Nr. 43);

5-t-butyl-3-[7-fluoro-3,4-dihydro-4-(prop-2-ynyl)-2H-1,4-benzoxazin-3-onyl]-1,3,4-thiadiazol-2(3H)-one (compound Nr. 44);

5-t-butyl-3-[2-chloro-5-(prop-2-ynyloxy)phenyl]-1,3,4-thiadiazol-2(3H)-one (compound Nr. 45);

5-t-butyl-3-[4-chloro-5-(prop-2-ynyloxy)phenyl]-1,3,4-thiadiazol-2(3H)-one (compound Nr. 46);

3-[2-bromo-4-chloro-5-(prop-2-ynyloxy)phenyl]-5-t-butyl-1,3,4-thiadiazol-2(3H)-one (compound Nr. 47);

5-t-butyl-3-(2,4-dichloro-5-isopropoxyphenyl)-1,3,4-thiadiazol-2(3H)-one (compound Nr. 48);

5-t-butyl-3-[2-chloro-4-cyano-5-(prop-2-ynyloxy)phenyl]-1,3,4-thiadiazol-2(3H)-one (compound Nr. 49);

5-t-butyl-3-[2-chloro-5-(prop-2-ynyloxy)-4-trifluoromethylphenyl]-1,3,4-thiadiazol-2(3H)-one (compound Nr. 50).

EXAMPLE 4

Preparation of 5-t-butyl-3-(2,4-dichloro-5-hydroxyphenyl) -1,3,4-thiadiazol-2(3H)-one (compound Nr. 51)

11.7 g of 5-t-butyl-3-(2,4-dichloro-5-isopropoxyphenyl)-1,3,4-thiadiazol-2(3H)-one (compound Nr. 48; 32.4 mmoles) and 250 ml of methylene chloride are charged into a 500 ml flask in a nitrogen atmosphere. AlCl$_3$ (12.9 g; 96.7 mmoles) is added to this solution in portions and the mixture is maintained under stirring at room temperature for 2 hours. The mixture is then carefully poured into 100 g of ice to which 100 ml of a saturated solution of sodium chloride have been added. 200 ml of ethyl ether are added and, after separation of the phases, the organic phase is washed with a saturated solution of sodium chloride, anhydrified with sodium sulfate and concentrated with a rotavapor. 10 g of the desired product are obtained having m.p. 130°–132° C.

EXAMPLE 5

Determination of the herbicidal activity in post-emergence.

The herbicidal activity of Compounds 1, 2, 7 and 15 was evaluated against both monocotyledon and dicotyledon weeds, in post-emergence treatment compared to 5-amino-3-phenyl-1,3,4-thiadiazol-2(3H)-one (RC), corresponding to the compound of example 2 of U.S. Pat. No. 3.746.719 [therein called 4-phenyl-2-amino-1,3,4-thiadiazolone-(5)].

The evaluation tests of each product were carried out according to the following operating procedures.

The following weeds were sown in jars (diameter of more than 10 cm, height 10 cm) containing sandy earth (10 jars for each species):

dicotyledon: *Abutilon theofrasti* (AT), *Amaranthus retroflexus* (AR), *Chenopodium album* (CA), *Convolvulus sepium* (CS), *Ipomea purpurea* (IP), *Polygonum persicaria* (PP), *Portulaca oleracea* (PO), *Solanum nigrum* (SN)

monocotyledon: *Alopecurus myosuroides* (AM), *Digitaria sanquinalis* (DS), *Panicum dichotomiflorum* (PD), *Setaria viridis* (SV)

Water was added to each jar in a suitable quantity for a good germination of the seeds.

The jars were divided into two groups each containing 5 jars for each weed.

The first group of jars was treated fifteen days after sowing, i.e. when the weeds, depending on the species, were 10–15 cm high, with a hydroacetonic dispersion containing the product under examination at the desired concentration, acetone (10% by volume) and Tween 20 (0.5%).

The second group was only treated with a hydroacetonic solution containing acetone (10% by volume) and Tween 20 (0.5%), and was used as a comparison (control).

All the jars were uniformly watered every two days and kept in a conditioned environment under the following conditions:

temperature: 24° C.;

relative humidity: 60%;

photoperiod: 16 hours;

luminous intensity: 10000 lux.

Fifteen days after the treatment the herbicidal activity was evaluated on the basis of the following scale of values referring to the percentage of damage found on the plants which had been treated compared to those not treated (control):

0=0%–9% of damage;
1=10–29% of damage;
2=30%–49% of damage;
3=50%–69% of damage;
4=70%–89% of damage;
5=90% of damage-death of the plant treated.

The results obtained are shown in Table 1 below.

TABLE 1

HERBICIDAL ACTIVITY IN POST-EMERGENCE AT A DOSAGE OF 150 g/HA

| SPECIES | COMPOUND | | | | |
|---|---|---|---|---|---|
| | 1 | 2 | 7 | 15 | RC |
| AT | 5 | 5 | 5 | 5 | 0 |
| AR | 5 | 5 | 5 | 5 | 0 |
| CA | 5 | 5 | 5 | 5 | 1 |
| CS | 5 | 5 | 5 | 5 | 0 |
| IP | 5 | 5 | 5 | 5 | 1 |
| PP | 5 | 2 | 5 | 5 | 0 |
| PO | 5 | 5 | 5 | 5 | 0 |
| SN | 5 | 5 | 5 | 5 | 1 |
| AM | 5 | NT | NT | NT | 0 |
| DS | 5 | NT | NT | NT | 0 |
| PD | 5 | NT | NT | NT | 0 |
| SV | 5 | NT | NT | NT | 0 |

NT = not tested

EXAMPLE 6

Determination of the herbicidal activity in pre-emergence

The herbicidal activity of Compounds 1, 7, 8, 9, 14, 15 and 17 was evaluated against both monocotyledon and dicotyledon weeds, and against some important crops, in pre-emergence treatment compared to 5-amino-3-phenyl-1,3,4-thiadiazol-2(3H)-one (RC), corresponding to the compound of example 2 of U.S. Pat. No. 3.746.719.

The evaluation tests of each product were carried out according to the following operating procedures.

The following weeds and crops were sown in jars (diameter of more than 10 cm, height 10 cm) containing sandy earth (10 jars for each species):

dicotyledon: *Amaranthus retroflexus* (AR), *Chenopodium album* (CA), *Capsella bursa pastoris* (CB), *Papaver rhoaes* (PR), *Portulaca oleracea* (PO), *Solanum nigrum* (SN)

monocotyledon: *Digitaria sanquinalis* (DS), *Echinochloa crusgalli* (EC), *Panicum dichotomiflorum* (PD)

crops: rice (*Oryza sativa*), maize (*Zea mays*), soybean (*Glycine max*), wheat (*Triticum spp.*)

The jars were divided into two groups each containing 5 jars for each weed and crop.

24 hours after sowing, the first group of jars was dampened with a light shower and, an hour after watering, treated with a hydroacetonic dispersion containing the product under examination at the desired concentration, acetone (10% by volume) and Tween 20 (0.5%).

The second group was only treated with a hydroacetonic solution containing acetone (10% by volume) and Tween 20 (0.5%), and was used as a comparison (control).

After the treatment all the jars were uniformly watered every two days and kept in a conditioned environment under the following conditions:

temperature: 24° C.;

relative humidity: 60%;

photoperiod: 16 hours;

luminous intensity: 10000 lux.

28 days after the treatment the herbicidal activity was evaluated on the basis of the following scale of values referring to the percentage of damage found on the plants which had been treated compared to those not treated (control):

0=0%–9% of damage;
1=10–29% of damage;
2=30%–49% of damage;
3=50%–69% of damage;
4=70%–89% of damage;
5=90% of damage-death of the plant treated.

The results obtained are shown in Table 2 below.

TABLE 2

HERBICIDAL ACTIVITY IN PRE-EMERGENCE AT A DOSAGE OF 150 G/HA

| SPECIES | COMPOUND | | | | | | | |
|---|---|---|---|---|---|---|---|---|
| | 1 | 7 | 8 | 9 | 14 | 15 | 17 | RC |
| AR | 5 | 5 | 5 | 5 | 5 | 5 | 5 | 0 |
| CA | 5 | 5 | 5 | 5 | 5 | 5 | 5 | 0 |
| CB | 5 | 5 | 5 | 5 | 5 | 5 | 5 | 0 |
| PR | 5 | 5 | 5 | 5 | 5 | 5 | 5 | 0 |
| PO | 5 | 5 | 5 | 3 | 5 | 5 | 1 | 0 |
| SN | 5 | 4 | 5 | 5 | 5 | 5 | 5 | 0 |
| DS | 5 | 5 | 5 | 5 | 5 | 5 | 5 | 0 |
| EC | 5 | 5 | 4 | 5 | 5 | 5 | 5 | 0 |
| PD | 5 | 5 | 5 | 5 | 5 | 5 | 5 | 0 |

TABLE 2-continued

HERBICIDAL ACTIVITY IN PRE-EMERGENCE
AT A DOSAGE OF 150 G/HA

| | COMPOUND | | | | | | | |
|---|---|---|---|---|---|---|---|---|
| | 1 | 7 | 8 | 9 | 14 | 15 | 17 | RC |
| RICE | 0 | 0 | NT | 0 | 1 | 0 | 0 | 0 |
| MAIZE | 0 | 1 | NT | 0 | 0 | NT | 0 | 0 |
| SOYBEAN | 0 | 1 | NT | 0 | 0 | NT | 0 | 0 |
| WHEAT | 0 | 0 | NT | 0 | 0 | NT | 1 | 0 |

NT = not tested

We claim:
1. An arylthiadiazolone of general formula (I):

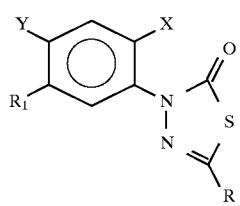

wherein:
R represents a $C_1$–$C_6$ alkyl or haloalkyl group, linear or branched; a $C_3$–$C_6$ cycloalkyl or halocycloalkyl group; a $C_4$–$C_7$ cycloalkylalkyl or halocycloalkylalkyl group; or a $C_2$–$C_6$ alkenyl or haloalkenyl group, linear or branched;

X represents a hydrogen atom; a fluorine atom; a chlorine atom; a bromine atom; or a methyl group;

Y represents a hydrogen atom, chlorine, fluorine, bromine or iodine; a $C_1$–$C_4$ alkyl or haloalkyl group, linear or branched; a $C_1$–$C_4$ alkoxy or haloalkoxy group, linear or branched; a $C_1$–$C_4$ alkylthio or haloalkylthio group, linear or branched; a $C_1$–$C_4$ alkylsulphonyl group, linear or branched; a $C_1$–$C_4$ alkylsulphinyl groups linear or branched; a cyano group; or a nitro group;

$R_1$ represents a $C_1$–$C_8$ alkyl group, linear or branched; a $C_1$–$C_8$ alkoxy group, linear or branched; a $C_1$–$C_8$ alkylthio group, linear or branched; a $C_3$–$C_6$ cycloalkoxy group; a $C_3$–$C_6$ cycloalkylthio group; a $C_4$–$C_8$ cycloalkylalkyl group; a $C_4$–$C_8$ cycloalkylalkoxy group; a $C_4$–$C_8$ , cycloalkylalkylthio group; a $C_2$–$C_8$ alkenyl group, linear or branched; a $C_2$–$C_8$ alkenyloxy group, linear or branched; a $C_2$–$C_8$ alkenylthio group, linear or branched; a $C_2$–$C_8$ alkynyl group, linear or branched; a $C_3$–$C_8$ alkynyloxy group, linear or branched; a $C_3$–$C_8$ alkynylthio group, linear or branched; a $C_3$–$C_8$ alkynylsulphinyl group, linear or branched; a $C_3$–$C_8$ alkynylsulphonyl group, linear or branched; an OH group; or an SH group; said groups in turn optionally substituted with one or more groups selected from chlorine, fluorine, bromine, iodine, $C_1$–$C_4$ alkyl or haloalkyl groups, linear or branched; $C_1$–$C_4$ alkoxy or haloalkoxy groups, linear or branched; and $C_1$–$C_4$ alkylthio or haloalkylthio groups, linear or branched;

or, Y and $R_1$, jointly represent an O—$CH_2$—CO—$NR_4$ group wherein $R_4$ represents a hydrogen atom; a $C_1$–$C_8$ alkyl or haloalkyl group, linear or branched; a $C_4$–$C_8$ cycloalkylalkyl or halocycloalkylalkyl group; a $C_2$–$C_8$ alkenyl or haloalkenyl group, linear or branched; a $C_3$–$C_8$ alkynyl or haloalkynyl group, linear or branched; or a $C_5$–$C_8$ alkoxyalkynyl or haloalkoxyalkynyl group, linear or branched.

2. The arylthiadiazolone according to claim 1, consisting of 5-t-butyl-3-(2,4-dichloro-5-prop-2-ynyloxy)phenyl-1,3,4-thiadiazol-2(3H)-one.

3. The arylthiadiazolone according to claim 1, consisting of 5-t-butyl-3-[5-(but-3-yn-2-yloxy)-2,4-dichlorophenyl]-1,3,4-thiadiazol-2-(3H)-one.

4. The arylthiadiazolone according to claim 1, consisting of 5-cyclopropyl-3-[2,4-dichloro-5-(prop-2-ynyloxy)-phenyl]-1,3,4-thiadiazol-2-(3H)-one.

5. The arylthiadiazolone according to claim 1, consisting of 3-[5-(but-3-yn-2-yloxy)-2,4-dichlorophenyl]-5-cyclopropyl-1,3,4-thiadiazol-2(3H)-one.

6. The arylthiadiazolone according to claim 1, consisting of 5-cyclopropyl-3-[4-cloro-2-fluoro-5-(prop-2-ynyloxy)phenyl]-1,3,4-thiadiazol-2(3H)-one.

7. The arylthiadiazolone according to claim 1, consisting of 3-[4-chloro-2-fluoro-5-(prop-2-ynyloxy)phenyl]-5-ethyl-1,3,4-thiadiazol-2(3H)-one.

8. The arylthiadiazolone according to claim 1, consisting of 3-[2,4-dichloro-5-(prop-2-ynyloxy)phenyl]-5-isopropyl-1,3,4-thiadiazol-2(3H)-one.

9. The arylthiadiazolone according to claim 1, consisting of 3-[4-chloro-2-fluoro-5-(prop-2-ynyloxy)phenyl]-5-isopropyl-1,3,4-thiadiazol-2(3H)-one.

10. A process for the preparation of an arylthiadizolone according to claim 1, which comprises the reaction of a thiohydrazide having general formula (II):

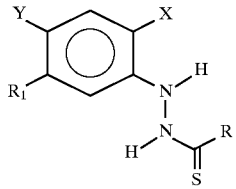

wherein R, X, Y and $R_1$ have the same meanings described in claim 2 with a cyclizing agent having general formula (III):

wherein:
L represents a chlorine atom; a $C_1$–$C_4$ alkoxy groups linear or branched; or a phenoxy group;

L' represents a chlorine atom; a $C_1$–$C_4$ alkoxy group, linear or branched: or a phenoxy group; or, when L represents a chlorine atom, L' represents a trichloromethoxy group or a benzyloxy group.

11. The process according to claim 10, wherein the cyclizing agent having general formula (III) is selected from phosgene, trichloromethylchloroformate (diphosgene), alkylchloroformate, benzylchloroformate, and phenylchloroformate.

12. The process according to claim 11, wherein the cyclizing agent having general formula (III) is phosgene or trichloromethylchloroformate and the cyclization reaction is carried out in a single step.

13. The process according to claim 10, wherein the thiohydrazide having general formula (II), dissolved or suspended in a suitable inert organic solvent, is treated with the cyclizing agent, optionally dissolved in turn in a suitable inert organic solvent, at a temperature of between 20° C. and the boiling point of the mixture itself, optionally in the presence of an inorganic or organic base.

14. The process according to claim 13, wherein the inert organic solvents are selected from chlorinated hydrocarbons, aromatic hydrocarbons, chlorinated aromatic hydrocarbons, ethers, and esters.

15. The process according to claim 13, wherein the inorganic base is sodium bicarbonate, sodium hydroxide, sodium carbonate, sodium hydride, potassium hydroxide, or potassium carbonate.

16. The process according to claim 13, wherein the organic base is selected from triethylamine, pyridine, and 4-dimethylaminopyridine.

17. The process according to claim 10, wherein the cyclizing agent having general formula (III) is an alkyl, benzyl or phenylchloroformate and the cyclization reaction is carried out in two steps.

18. The process according to claim 17, wherein the thiohydrazide having general formula (II), dissolved or suspended in an inert organic solvent selected from the group consisting of chlorinated hydrocarbons, aromatic hydrocarbons, chlorinated aromatic hydrocarbons, ethers, and esters is treated with the ester of chloroformic acid in the presence of an inorganic base selected from the group consisting of sodium bicarbonate, sodium hydroxide, sodium carbonate, sodium hydride, potassium hydroxide, and potassium carbonate or an organic base selected from the group consisting of triethylamine, pyridine, and 4-dimethylaminopyridine at a temperature of between 0° C. and the boiling point of the mixture itself, obtaining the intermediate having general formula (IV):

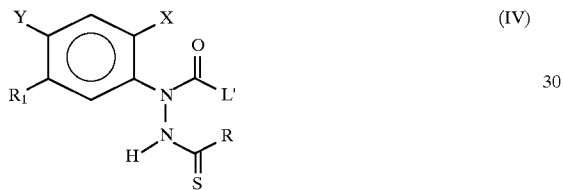

(IV)

wherein R represents a $C_1$—$C_6$ alkyl or haloalkyl group, linear or branched, a $C_3$—$C_6$ cycloalkyl or halocycloalkyl group; a $C_4$—$C_7$ cycloalkylalkyl or halocycloalkylalkyl group; or a $C_2$—$C_6$ alkenyl or haloalkenyl group linear or branched;

X represents a hydrogen atom; a fluorine atom: a chlorine atom: a bromine atom, or a methyl group:

Y represents a hydrogen atom chlorine, fluorine, bromine or iodine; a $C_1$—$C_4$ alkyl or haloalkyl group, linear or branched; a $C_1$—$C_4$ alkoxy or haloalkoxy group, linear or branched; a $C_1$—$C_4$ alkylthio or haloalkylthio group, linear or branched; a $C_1$—$C_4$ alkylsulphonyl group, linear or branched, a $C_1$—$C_4$ alkylsulphinyl group, linear or branched; a cyano group; or a nitro group;

$R_1$ represents a $C_1$—$C_8$ alkyl group, linear or branched; a $C_1$—$C_8$ alkoxy group, linear or branched; a $C_1$—$C_8$ alkylthio group, linear or branched; a $C_3$—C6 cycloalkoxy group; a $C_3$—$C_6$ cycloalkylthio group; a $C_4$—$C_8$ cycloalkylalkyl group; a $C_4$—$C_8$ cycloalkylalkoxy group; a $C_4$—$C_8$ cycloalkylalkylthio group; a $C_2$—$C_8$ alkenyl group, linear or branched; a $C_2$—$C_8$ alkenyloxy group, linear or branched: a $C_2$—$C_8$ alkenylthio group, linear or branched; a $C_2$—$C_8$ alkynyl group, linear or branched; a $C_3$—$C_8$ alkynyloxy group, linear or branched; a $C_3$—$C_8$ alkynylthio group, linear or branched; a $C_3$—$C_8$ alkynylsulphinyl group, linear or branched; a $C_3$—$C_8$ alkynylsulphonyl group, linear or branched; an OH group; or an SH group; said groups in turn optionally substituted with one or more groups selected from chlorine, fluorine, bromine, iodine, $C_1$—$C_4$ alkyl or haloalkyl groups, linear or branched; $C_1$—$C_4$ alkoxy or haloalkoxy groups, linear or branched; and $C_1$—$C_4$ alkylthio or haloalkylthio groups, linear or branched;

or, Y and $R_1$, jointly represent an O—$CH_2$—CO—$N_4$ group wherein $R_4$ represents a hydrogen atom: a $C_1$—$C_8$ alkyl or haloalkyl group, linear or branched; a $C_4$—$C_8$ cycloalkylalkyl or halocycloalkylalkyl group; a $C_2$—$C_8$ alkenyl or haloalkenyl group, linear or branched; a $C_3$—$C_8$ alkynyl or haloalkynyl group, linear or branched; or a $C_5$—$C_8$ alkoxyalkynyl or haloalkoxyalkynyl group, linear or branched and L' represents a $C_1$—$C_4$ alkoxy group, linear or branched, a phenoxy group or a benzyloxy group, which is subsequently cyclized by heating to a temperature of between 120° C. and 200°, optionally in the presence of a high-boiling organic solvent and a base.

19. The process according to claim 18, wherein the high-boiling organic solvent is selected from xylene and ortho-dichlorobenzene.

20. The process according to claim 18, wherein the base is 4-dimethylaminopyridine.

21. An herbicide containing one or more arylthiadiazolones according to claim 1, alone or in the presence of solid carriers, liquid diluents, surfactants or other active ingredients.

22. The herbicide according to claim 21, wherein the concentration of active substance is between 1% and 90%.

23. A method for controlling weeds in cultivated areas which consists in applying the herbicide according to claim 21 to these areas.

* * * * *